United States Patent [19]

Samuels et al.

[11] 4,201,314
[45] May 6, 1980

[54] CARTRIDGE FOR A SURGICAL CLIP APPLYING DEVICE

[76] Inventors: Peter B. Samuels, 14708 Sutton St., Sherman Oaks, Calif. 91403; Ernest C. Wood, 2461 Ivanhoe Dr., Los Angeles, Calif. 90039

[21] Appl. No.: 871,532

[22] Filed: Jan. 23, 1978

[51] Int. Cl.² ............................................. B65H 1/12
[52] U.S. Cl. ..................................... 221/198; 29/816; 221/227
[58] Field of Search ....................... 221/198, 227, 279; 29/816

[56] References Cited

U.S. PATENT DOCUMENTS

| 2,902,196 | 9/1959 | Gray | 221/227 X |
| 3,775,825 | 12/1973 | Wood et al. | 29/816 X |
| 3,891,014 | 6/1975 | Gunn | 221/279 X |

Primary Examiner—F. J. Bartuska
Attorney, Agent, or Firm—McDougall, Hersh & Scott

[57] ABSTRACT

A cartridge is disclosed suitable for use in a surgical clip applicator. The cartridge includes a pair of channels for the receipt of a supply of clips. A clip pusher is biased toward the clip supply by a spring in order to feed the clips forwardly. Movement of the pusher is arrested or permitted by operation of a switch button which controls a triangular locking member. In a first position the locking member engages the bottom of the cartridge to prevent forward movement while in a second position the locking member permits forward movement of the pusher.

10 Claims, 5 Drawing Figures

CARTRIDGE FOR A SURGICAL CLIP APPLYING DEVICE

BACKGROUND OF THE INVENTION

This invention relates to the field of medical appliances and instruments utilized by surgeons. More specifically, it relates to a class of surgical instruments utilized by the medical profession to perform abdominal surgery and similar surgical procedures in an efficient manner. During such surgery it is often necessary to utilize a large number of sutures to close the incision. In order to increase the rate at which the sutures can be applied, devices have been developed which apply surgical clips to the ends of sutures rather than requiring a surgeon to individually knot the end of each suture. Such devices include the applicator disclosed in U.S. Pat. No. 3,775,825. Such an applicator applies clips to a suture at two adjacent points and then severs the suture between the clips. In this manner one suture is completely secured while the end of the next suture is prepared for the next stitch.

In the device disclosed in the referenced U.S. patent, a manually operable clip cartridge is disclosed in which the cartridge stores parallel columns of clips prior to their delivery to the jaws of the applicator device. The manually operated pusher there disclosed, however, often resulted in empty applier jaws resulting in a cut suture without a clip provided on the cut end thereof. In order to accurately feed the suture clips to the applier jaws, it was necessary to manually maintain a proper amount of pressure on the pusher to position the clips in the jaws and then maintain the pressure during the crimping of the clips to prevent the clips from moving out from beneath the jaws prior to the time that they are secured to the suture. Thus, there is a desire to improve the clip cartridge so that the surgeon utilizing the applicator need not maintain manual pressure on the pusher in order to successfully apply clips. This improves the rate at which the clips may be applied and significantly decreases the failure rate of the applicator device.

It is accordingly an object of the present invention to provide an automatic clip cartridge which need not be manually operated during the application of clips by the applicator device.

It is a further object of the present invention to provide a clip cartridge which automatically maintains pressure on the cartridge pusher to maintain the clips in the proper position for crimping by the applicator tool.

Another object of the present invention is to provide a clip cartridge which is more convenient and easy to load and use and which permits removal of the clip cartridge prior to its becoming empty to permit cleaning or reloading.

A further object of the invention is to provide a clip cartridge employing a locking member which is selectively operated to permit the pusher to apply pressure against the clips or to prevent such pressure from being applied when it is desired to remove the cartridge from the applicator.

Other objects and advantages of the invention will be apparent from the remaining portion of the specification.

PRIOR ART STATEMENT

The closest prior art of which applicant is aware is U.S. Pat. No. 3,775,825 to Wood et al. As indicated in the background portion of the specification, this patent discloses a clip applicator and a manually operated clip cartridge. The clip cartridge of the present invention is suitably designed for use with the clip applicator disclosed in the referenced patent.

DETAILED DESCRIPTION

Figure 1:
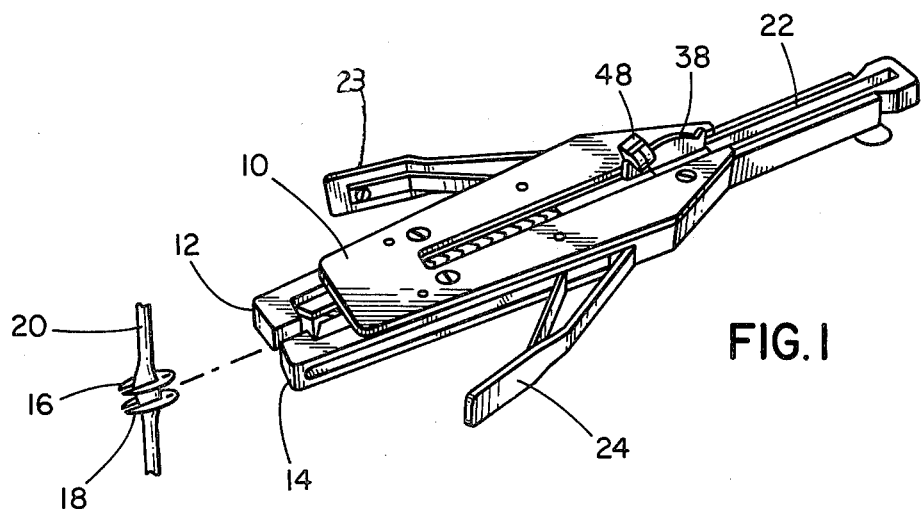
FIG. 1 is a perspective view of a clip applicator having the clip cartridge of the present invention installed therein.

Referring to FIG. 1, a suture applicator is illustrated of the type suitable for use with the clip cartridge according to the present invention. The clip applicator 10 includes a pair of opposed jaws 12 and 14 which crimp a pair of clips 16 and 18 onto a suture 20 passed between the jaws. The jaws are actuated by manual pressure on handles 23 and 24. Applicator 10 may also include means for severing that portion of the suture located between the clips 16 and 18. The clips are supplied to the jaws from a clip cartridge 22 received in the applicator 10. The clip applicator illustrated in FIG. 1 is substantially identical to the applicator disclosed and claimed in U.S. Pat. No. 3,775,825 hereby incorporated by reference. The reader is referred to that patent for additional details of the applicator.

Figure 2:
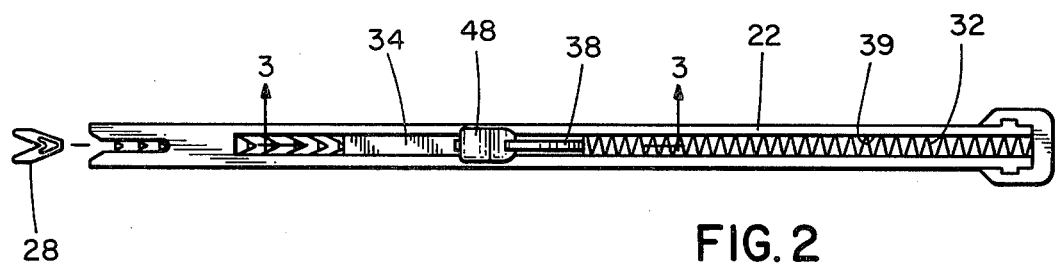
FIG. 2 is a plan view of the clip applicator according to the invention.

Referring to FIGS. 2 through 5, the clip cartridge 22 according to the present invention is illustrated. Unlike the cartridge of the prior art, the present invention is capable of applying a constant force to the supply of clips provided in the cartridge so as to index clips after each crimping operation and to maintain them properly positioned between the jaws of the applicator both before and during the crimping process. The cartridge 22 is provided with an upper clip channel 24 and a lower clip channel 26, said channels being generally parallel to and spaced from each other in a horizontal plane. These channels are adapted to receive a plurality of clips such as clip 28. The clips are received in the channels in an uncrimped condition, as illustrated in FIG. 2, and are applied to the suture by being crimped thereon by the applicator 10. It will be apparent that if desired for a special application the cartridge could be provided with only a single clip channel.

A clip pusher member 30 is provided for urging the clips in the upper and lower channels forwardly under urging of the pusher spring 32. The pusher 30 has channel members 34 36 dimensioned to fit within the channels 24 and 26 for that purpose. Attached to the pusher member at the rear portion thereof is a cam plate 38 which extends from the cartridge bottom upwardly through a slot 39 in the top of the cartridge. The lower portion of the cam plate 38 is received in the cartridge and has an inverted V-shaped configuration including walls 40 and 42. These walls in conjunction with the cartridge bottom 44 define a triangular shaped recess in which a locking member 46 is provided.

Locking member 46 is triangular in shape and appropriately dimensioned for movement within the recess. The locking member is preferably formed of metal and may be as shown or a solid triangle is also satisfactory. It is movable within the recess between the two positions illustrated in FIGS. 3 and 5. The locking member 46 is attached to a switch button 48 by means of a wire spring member 50. The spring member is attached to a central point of the locking member as by being received in an aperture therethrough and also secured to the switch button in a manner best illustrated in FIG. 4. The switch button is provided with a T-shaped slot 52 for receiving the upper end of the spring member, which end is bent into the configuration illustrated in FIG. 3 to maintain tension on the locking member. As a result the locking member is resiliently biased upwardly against the top of the cam plate 38.

The switch button 48 is provided with a lower channel 49 dimensioned to permit the switch button to ride on the top of the cam plate 38. Thus, the switch button is movable between the forward position illustrated in FIG. 3 and the rearward position illustrated in FIG. 5. By virtue of the bias of the spring member 50 on the locking member 46, the movement of the switch button between the forward and rear positions is effective for causing the locking member 46 to pivot between the positions illustrated in FIGS. 3 and 5, respectively.

Figure 3:
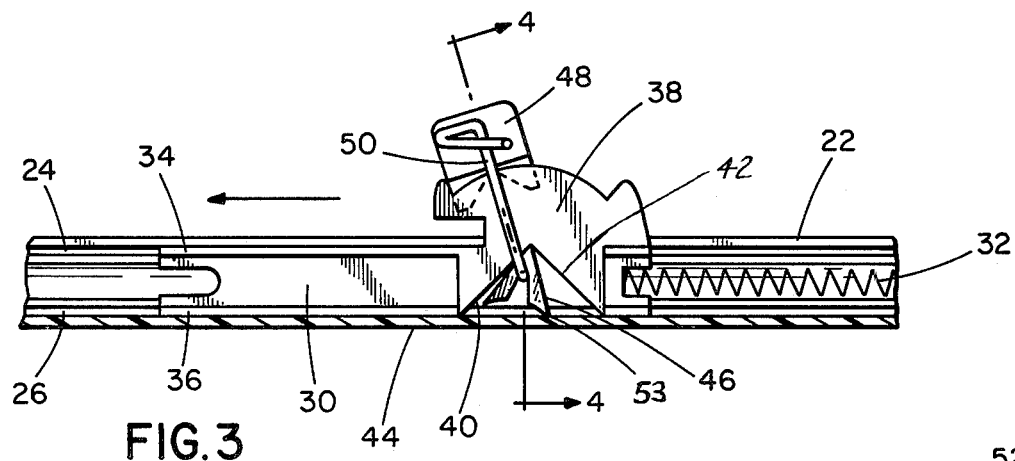
FIG. 3 is a sectional view along the lines 3—3 of FIG. 2 illustrating the locking member in its unlocked position.
Figures 4, 5:
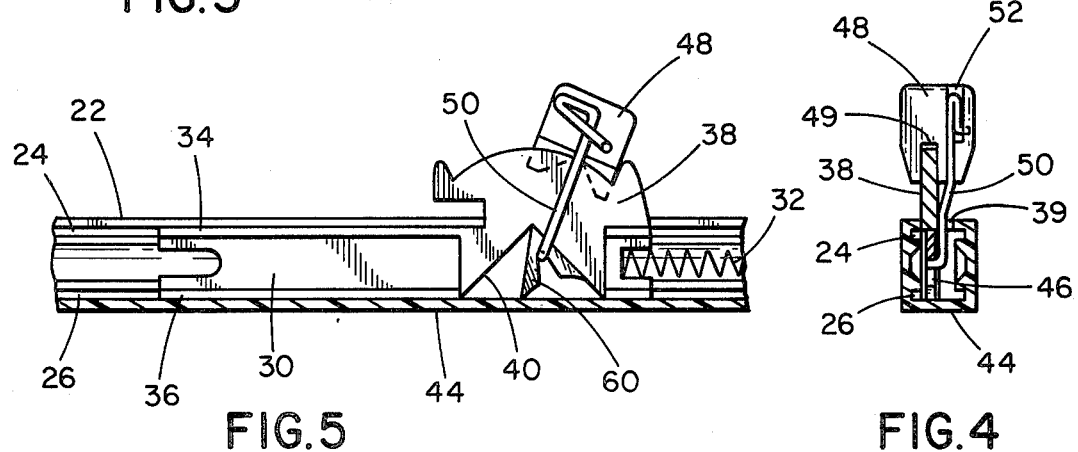
FIG. 4 is a sectional view along the lines 4—4 of FIG. 3.
FIG. 5 is a view similar to FIG. 3 illustrating the locking member in its locked position.

In the FIG. 3 position the rear point 53 of the locking member is in contact with the clip bottom 44. This does not obstruct forward movement of the pusher member 30 in response to the spring 32. In this case the locking member merely trails along as the clip pusher moves forward after each application of a pair of clips to index the next pair of clips into the jaws 12 and 14. In the position illustrated in FIG. 5, however, the forward point 60 of the locking member is in contact with the bottom of the clip cartridge. In that case the edge engages the clip bottom 44 and prevents forward motion of the pusher member 30 in spite of the spring 32.

The cartridge is loaded into the applicator 10 in a conventional manner as described in the aforementioned U.S. Pat. No. 3,775,825. During loading the switch button 48 is maintained in the rearward position illustrated in FIG. 5. Under those circumstances, the forward point 60 of the locking member is in locking engagement with the cartridge bottom 44. After the cartridge has been snapped in place the switch button 48 is moved to the forward position illustrated in FIG. 3. Movement of the switch button to the forward position, however, does not immediately release the pusher member 30 inasmuch as the locking member will not disengage because of the force from the pusher spring 32.

In order to disengage the forward point 60 of the locking member, a slight rearward pressure is applied to the cam plate 38 as, for example, by use of the index finger or thumb. As soon as the force of the spring 32 is overcome, spring member 50 is enabled to exert upward pressure on the locking member sufficient to flip it from the position shown in FIG. 5 to the position shown in FIG. 3. Stated differently, the locking member will move from a position in intimate contact with wall 42 to the position wherein it is in intimate contact with wall 40 of the cam plate. In the FIG. 3 position the pusher spring 32 is then free to cause forward motion of the pusher 30 to successively index clips into the jaws of the applicator and to maintain the clips in proper position before and during clip application.

If, for some reason, it is desired to remove the clip cartridge prior to exhausting all clips therein or if there should be a jam in the clip channel the process described is merely reversed. That is, the switch button 48 is moved from the FIG. 3 position to the FIG. 5 position. This causes the locking member 46 to immediately move to the FIG. 5 position by virtue of the fact that the force from spring 32 does not oppose movement of the rear point. As soon as the front point engages the cartridge bottom the pusher is locked against further movement. The cartridge may then be removed from the applicator without the possibility of the unused clips being ejected from the cartridge by the pusher.

While I have shown and described embodiments of this invention in some detail, it will be understood that this description and illustrations are offered merely by way of example, and that the invention is to be limited in scope only by the appended claims.

I claim:

1. A cartridge for supplying surgical clips to the jaws of a clip applicator comprising:
    (a) a cartridge body having forward and rear ends and at least one clip channel for storing a plurality of said clips to be dispensed from said forward end to said jaws,
    (b) means for forwardly urging said clips in said channel,
    (c) means for selectively locking said urging means to prevent forward movement of clips in said channel, said locking means including a cam plate secured to said urging means for movement therewith, said plate having a recess provided in its lower portion, and a locking member pivotable between an unlocked position engaging a first portion of said cam plate and a locked position engaging a second portion of said cam plate and in which the locking member also engages the bottom of said cartridge, and
    (d) manually operated means for moving said locking member between said locked and unlocked positions.

2. The cartridge according to claim 1 wherein said cartridge includes two clip channels spaced from each other,
    said urging means simultaneously forwardly urging clips in both channels.

3. The cartridge according to claim 1 wherein said urging means includes:
    (a) a clip pusher dimensioned to be slidably received in said channel behind said plurality of clips,
    (b) spring means located between said pusher and said cartridge rear end for urging said pusher toward said forward end.

4. The cartridge according to claim 2 wherein said urging means includes:
    (a) a clip pusher dimensioned to be slidably received in said channels behind said plurality of clips,
    (b) spring means located between said pusher and said cartridge rear end for urging said pusher toward said forward end.

5. A cartridge for supplying surgical clips to the jaws of a clip applicator comprising:
    (a) a cartridge body having forward and rear ends and at least one clip channel for storing a plurality of said clips to be dispensed from said forward end to said jaws,
    (b) means for forwardly urging said clips in said channel, and (c) means for selectively locking said urging means to prevent forward movement of clips in said channel, said cartridge being provided with a vertical slot extending through the top of the cartridge to the cartridge bottom and wherein said locking means includes:

a cam plate secured to said urging means for movement therewith and positioned in said slot, said cam plate having an inverted V-shaped recess provided in its lower portion, a locking member provided in the space defined by said recess and the bottom of said cartridge movable between an unlocked position and a locked position in which the locking member engages the bottom of said cartridge, manually operated means for moving said locking member between said locked and unlocked positions.

6. The cartridge according to claim 5 wherein said moving means includes:

(a) a switch button supported on said cam plate for movement thereon between forward and rear positions relative to said cam plate, (b) a spring member connecting said locking member to said switch button and urging the former toward the latter whereby movement of said button to said forward position biases said locking member to said unlocked position while movement of said button to said rear position biases said locking member to said locked position.

7. The cartridge according to claim 5 wherein said locking member is triangular in shape and in said locked position the forward point of said member engages said cartridge bottom to prevent forward movement of said pusher and cam plate.

8. The cartridge according to claim 6 wherein said locking member is triangular in shape and in said locked position the forward point of said member engages said cartridge bottom to prevent forward movement of said pusher and cam plate.

9. The cartridge according to claim 8 wherein one end of said spring member is attached to said triangular locking member at the center point of the latter.

10. The cartridge according to claim 9 wherein said switch button is provided with a T-shaped slot and the other end of said spring member is received in said T slot and bent within said slot to urge the locking member toward the switch button.

* * * * *